United States Patent [19]

von Gentzkow et al.

[11] Patent Number: 5,389,533

[45] Date of Patent: Feb. 14, 1995

[54] IMMOBILIZATION OF BIOCHEMICAL SUBSTANCES ON A CARRIER CONTAINING A LAYER OF AN OLEFINIC - UNSATURATED, EPOXYFUNCTIONAL POLYETHER

[75] Inventors: Wolfgang von Gentzkow, Kleinsendelbach; Hans-Dieter Feucht, Renningen, both of Germany

[73] Assignee: Siemens Aktiengesellschaft, Munich, Germany

[21] Appl. No.: 34,319

[22] Filed: Mar. 22, 1993

[30] Foreign Application Priority Data

Mar. 23, 1992 [DE] Germany ............... 4209369

[51] Int. Cl.⁶ .................. C12N 11/08; C12N 11/06; G01N 33/545; G01N 33/549
[52] U.S. Cl. .................. 435/180; 435/176; 435/177; 435/181; 436/531; 436/532; 530/815; 530/816
[58] Field of Search ............... 435/174, 176, 177, 180, 435/181; 436/531, 532; 530/413, 815, 816

[56] References Cited

U.S. PATENT DOCUMENTS

| | | | |
|---|---|---|---|
| 3,844,892 | 10/1974 | Matthews | 435/181 |
| 3,853,708 | 12/1974 | Poratah et al. | 435/181 |
| 3,932,557 | 1/1976 | Matthews | 260/837 R |
| 4,268,423 | 5/1981 | Rohrbach et al. | 435/180 |
| 4,451,568 | 5/1984 | Schneider et al. | 435/181 |
| 4,612,288 | 9/1986 | Bigwood et al. | 435/180 |
| 5,109,089 | 4/1992 | Birkle et al. | 526/273 |

FOREIGN PATENT DOCUMENTS 0346865 12/1989 European Pat. Off. .

OTHER PUBLICATIONS

Hartmeier, W., "*Immobilisierte Biokatalysatoren*", Springer–Verlag Berlin, Heidelberg 1986, pp. 23–51.
Crueger, W. et al., "*Biotechnologie–Lehrbuch der angewandten Mikrobiologie*", R. Oldenbourg Verlag München, Wien 1989, pp. 201–203.
Woodward, J., "*Immobilised cells and enzymes*," IRL Press, Oxford, Washington, D.C. (1985), pp. 3–54.
Wiseman, Alan, PhD, FRSC, "*Handbook of Enzyme Biotechnology*, Second Edition", pp. 74–89 (1975).

*Primary Examiner*—David M. Naff
*Attorney, Agent, or Firm*—Kenyon & Kenyon

[57] ABSTRACT

Biochemical substances such as enzymes are immobilized by reaction with epoxy groups of an olefinic-unsaturated, epoxyfunctional polyether. Prior to immobilization, the polyether is applied to a carrier and cross-linked by treatment with high-energy radiation or peroxide to form a layer. After reacting the biochemical substance with epoxy groups, non-reacted epoxy groups are reacted with a compound containing an amino group and/or a carboxyl group such as an amino acid. Before immobilizing of the biochemical substance and after crosslinking, the polyether may be hydrophilized by reacting some of the epoxy groups with a hydrophilic compound such as an amino acid.

18 Claims, No Drawings

IMMOBILIZATION OF BIOCHEMICAL SUBSTANCES ON A CARRIER CONTAINING A LAYER OF AN OLEFINIC - UNSATURATED, EPOXYFUNCTIONAL POLYETHER

FIELD OF THE INVENTION

The invention relates to a method for immobilization of biochemical substances, particularly enzymes.

BACKGROUND OF THE INVENTION

Because of their selectivity and high level of catalytic activity, enzymes are increasingly being used in many sectors of the food, pharmaceutical and chemical industries, for the production and analysis of products, as well as in medicine for diagnosis and therapy. Although enzymes are not used up in the conversion which they catalyze, they cannot be reused, because of their substrate solubility. This brings a number of disadvantages with it, and attempts have been made for quite some time to overcome these by using immobilized enzymes.

Immobilization is understood to be the transformation of water-soluble enzymes into a form insoluble in water, while maintaining their catalytic effectiveness. This is possible by chemical and/or physical binding of the water-soluble enzymes to a carrier insoluble in water, as well as by inclusion in gel matrices or microcapsules which are insoluble water. The use of immobilized enzymes is limited, as a matter of principle, to processes with aqueous substrates or liquid substrates that contain water. The significant advantages of immobilized enzymes consist of the ease in separating them from the reaction solution and in the fact that they can be reused. These advantages result in significant cost savings, particularly in the case of enzymes which are not easily accessible and can be produced only in small yield. Since the end products remain free of enzymes, the heat treatment for inactivation of dissolved enzymes, which is necessary otherwise, is also eliminated, which is particularly advantageous in the case of heat-sensitive products. In addition, it is possible to use a continuous process with precise process control when using immobilized enzymes.

Every method with immobilized enzymes is in competition with the same method with dissolved enzymes. Immobilized enzymes are only competitive if clear economic advantages can be achieved with their use, for example in that improved and purer products are obtained, which can be processed more easily, faster and at lower cost.

For the immobilization of enzymes, the following methods have been known:
adsorption
ionic binding
absorption
covalent binding to a carrier surface
inclusion in a matrix or in microcapsules
inclusion by sheathing with a membrane (macroencapsulation)
cross-linking or copolymerization with difunctional or polyfunctional monomers.

However, all of these methods are not universally applicable. Only when the application of an enzyme has been precisely defined can a suitable carrier, the immobilization method and the reactor form be selected and coordinated with one another (see, for example: W. Hartmeier, "Immobilisierte Biokalaysatoren" ["Immobilized Biocatalysts"], Springer-Verlag Berlin, Heidelberg 1986, pages 23 to 51, and J. Woodward, "Immobilised cells and enzymes", IRL Press, Oxford, Washington DC, 1985, pages 3 to 54, as well as W. Crueger and A. Crueger, "Biotechnologie—Lehrbuch der angewandten Mikrobiologie ["Biotechnology—Handbook of Applied Microbiology"], R. Oldenbourg Verlag Munich, Vienna 1989, pages 201 to 203).

Physical adsorption of an enzyme on a carrier insoluble in water is the simplest and oldest method for immobilization of enzymes. It is based on non-specific physical interactions between the enzyme protein and the surface of the carrier material. The binding forces are mainly hydrogen bridges and van der Waals forces (see in this regard: S. A. Barker and I. Kay in "Handbook of Enzyme Biotechnology" (Editor: A. Wiseman), Ellis Horwood, Chichester 1975, Chapter 5, page 89). For immobilization, a concentrated enzyme solution is mixed with the carrier material. Carrier materials often used are activated charcoal, aluminum oxide, silicon dioxide, porous glass, cellulose and phenolic synthetic resins.

Adsorption has the disadvantage that because of the weak binding forces, desorption of the enzyme occurs over the period of use, by changes in temperature, pH or ionic strength, or due to the presence of other substances in the reaction solution. Another disadvantage is that adsorption is not specific, and thus further proteins or other substances can be adsorbed from the reaction solution. This can cause changes in the properties of the immobilized enzyme, and activity losses can occur.

In the case of ionic binding, the electrostatically charged enzyme molecule is attracted and fixed in place by a polyanionic or polycationic carrier with the opposite charge. As in the case of adsorption, again only a relatively weak bond occurs, since the charge of the enzyme protein is very small relative to its mass. The use of this method is also only possible for very low salt contents of the substrate solution, since other stronger ions can easily displace the enzyme molecules if they are present in the substrate. The ion exchanger resins which are most frequently used are DEAE cellulose (DEAE=diethylaminoethyl), DEAE Sephadex (an agarose preparation), and CM cellulose (CM=carboxymethyl). Also in the case of absorption in polymer layers, relatively unstable systems are obtained. Migration and extraction of the enzymes result in a constant decrease in activity and limit the lifetime of the enzyme layer.

Significantly more stable systems are achieved if the enzymes are covalently bound to a carrier surface, made insoluble via cross-linking or copolymerization, or are immobilized by microencapsulation or macroencapsulation. For the formation of covalent bonds and for cross-linking, free amino, carboxyl, hydroxyl and mercapto groups are available on the part of the enzymes. Both inorganic materials, such as glass, and natural and synthetic organic polymers can be used as the carrier material. A prerequisite in this connection is that the carrier materials contain reactive groups, such as isocyanate, isothiocyanate, acid chloride and epoxy groups. Less reactive groups can be activated, for example carboxyl groups can be activated using the carbodiimide or azide method, hydroxyl groups can be activated using the bromine cyan method, and amino groups can be activated using the isothiocyanate or azo method. It was possible, particularly on the basis of acrylic acid and methacrylic acid derivatives, to produce numerous reactive copolymers with dinitrofluorophenyl, isothiocyanate, oxirane or acid anhydride groups. Polyacrylamides with oxirane groups as well as modified copolymers on the basis of vinyl acetate and divinyl ethylene urea with oxirane groups are commercially available, for example.

Immobilization by cross-linking or by copolymerization represent special forms of covalent binding. In these methods, the formation of covalent bonds takes place between the enzyme molecules and difunctional or polyfunctional monomers, such as glutardialdehyde, or, in the case of copolymerization, additionally between the enzyme molecules and a polymerizing substance. In this manner, insoluble aggregates with a high molecular weight are formed. Cross-linking is generally used as an immobilization method in combination with one of the other methods, for example in combination with absorption or absorption. Here, the enzyme molecules are first absorbed on the surface of the carrier, or are absorbed in a layer located on it, and subsequently cross-linked.

A significant disadvantage of immobilization by covalent binding is the great stress on the biocatalysts connected with it. The immobilization procedures that are necessary, some of which are rough, in which a strong change in the pH occurs, organic solvents have to be used or reaction with reactive substances with a low molecular weight takes place, almost always lead to strong conformation changes and thus to activity losses of enzymes bound in such manner.

In immobilization by inclusion, i.e., microencapsulation or macroencapsulation, the enzymes themselves are not made insoluble, rather their reaction range is limited by semipermeable polymers or polymer layers. A prerequisite for the ability of enzymes sheathed in this manner to function is that substrates and products can pass through the sheathing substance, while the enzymes themselves have to be held back. In addition to natural polymers, such as alginate, carrageenan, pectin, agar and gelatin, which are, however, too large-meshed for permanent immobilization of enzymes, synthetic polymers, such as polyacrylamide, are particularly used for matrix sheathing. Polyamides, polyurethanes, polyesters and polyureas, for example, are used for encapsulation. The inclusion method has the disadvantage that relatively thick layers with long diffusion paths are formed.

SUMMARY OF THE INVENTION

It is an object of the invention to provide a method for immobilization of biochemical substances, which can be carried out in a technically simple, low-loss, efficient and low-cost manner, and which yields immobilized enzymes with a stable function and sufficient catalytic activity, in a reproducible manner.

This is accomplished, according to the invention, by applying an olefinic-unsaturated, epoxyfunctional polyether to a carrier material in the form of a layer. The polyether is cross-linked to form a large-mesh epoxyfunctional polymer matrix by means of high-energy radiation or using peroxide. The layer is treated with an aqueous solution of the biochemical substance, whereby the biochemical substance is immobilized in the polymer matrix by reaction with epoxy groups. Finally, the layer is stabilized by reaction of non-converted epoxy groups with a compound containing amino and/or carboxyl groups.

DETAILED DESCRIPTION OF THE INVENTION

The invention provides a new method for immobilization of enzymes and other biochemical substances, specifically in cross-linked epoxyfunctional polyethers. It was surprisingly found that these substances are able to penetrate into large-mesh cross-linked epoxyfunctional polyethers—from aqueous solution—and can be anchored in the polymer matrix, i.e., in the polymer network, under very mild conditions, by reaction with epoxy groups in chain position. This fact is completely new, and it opens up the possibility of very gentle immobilization. The method according to the invention is not limited to the immobilization of enzymes, but rather also allows for the immobilization of other biochemical substances, such as coenzymes, enzyme inhibitors, effectors and antibodies. Preferred embodiments of the inventive method will be described herein.

The method according to the invention includes the following steps, in general:

1. Coating of carrier materials

An epoxyfunctional polyether which can be cross-linked by radicals, or mixture of such polyethers is applied, in the desired layer thickness, to a carrier material, if necessary in combination with a cross-linking initiator, a cross-linking reinforcer and/or other additives. The carrier can consist of inorganic or organic material and be present in the form of fibers, non-woven material, paper or woven material, or in the form of planar materials. The use of porous or pore-free membrane materials can prove to be particularly advantageous. Depending on the application case and the flow behavior of the polyether used, coating can be carried out of a solution or without solvent, by dipping, spin-coating, roller-coating, curtain-coating or another conventional technical process, where it might be necessary to pretreat the carrier surface with an adhesion agent. In the case of material which extends lengthwise, continuous coating can take place. The layer thickness can be controlled by adjusting the viscosity and by adding a solvent or a reactive diluent. The layer produced in this manner must be freed of volatile components, in every case, which can be done by drying or degassing, for example. To improve the adhesion of the coating on the carrier surface, which has been treated with an adhesion agent, if necessary, a tempering step can prove to be advantageous.

2. Cross-linking of the coating

Cross-linking of the coating, i.e., the polyether, takes place by means of high-energy radiation, particularly UV, electron or γ radiation, or with peroxide. For cross-linking with peroxide, organic peroxides are brought into the polyether or into the polyether mixture. Cross-linking is initiated by thermal decomposition of the peroxides to form radicals. Heat transfer to the coating can take place by means of IR radiation, microwaves, heated rolling or pressing tools, or by means of hot gases. As a result of the cross-linking, during which only the olefin-unsaturated groups that can be polymerized by radicals are converted, while the epoxy groups are quantitatively maintained, a large-mesh polymer network is formed.

3. Immobilization of the biochemical substance

Upon contacting of the cross-linked layer with an aqueous solution of the biochemical substance, this substance migrates into the polymer matrix and is covalently bound there by reaction with the epoxy groups.

A prerequisite for this process, along with the necessary mesh width, is sufficient hydrophilicity of the polymer network formed during cross-linking. Immobilization can therefore be accelerated by prior hydrophilization of the polyether. This is done by conversion of part of the epoxy groups with hydrophilic compounds which contain reactive groups, such as NH, OH, SH or COOH groups, causing the hydrophilic character of the polymer layer to be increased. The immobilization process can also be significantly accelerated by means of additives, such as polyvinyl pyrrolidone, which result in increased water absorption of the polyethers, as well as by solvents which are miscible with water, such as dioxane, tetrahydrofuran, alcohols or polyethers. Furthermore, several different biochemical substances can also be immobilized in a single layer, and this can be done either simultaneously or consecutively.

4. Stabilization of the coating

This step includes the reaction of epoxy groups remaining after immobilization, with a compound containing amino and/or carboxyl groups, particularly an amino acid. Depending on the compound used, stabilization can be utilized to achieve closer cross-linking of the layer, and thus improved mechanical strength, or for adaptation of the material properties and the material transport. Furthermore, a superficial covering of this layer with one or more additional layers is possible, which might also be practical for adjusting defined diffusion conditions of the reaction partners and products to be converted.

For the method according to the invention, epoxyfunctional polyethers with the following structure are particularly suitable; these are the subject of the U.S. patent application Ser. No. 08/035,016—"Polyethers" which was filed on the same day as this application:

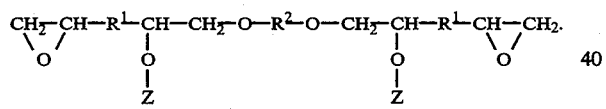

Here, the following applies:
Z=

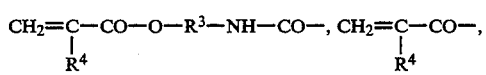

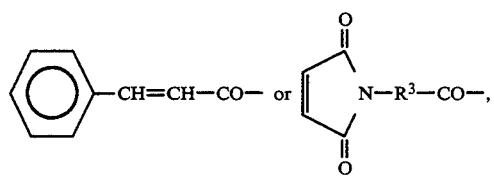

where
$R^3 = —(CH_2)_m—$, with m=1 to 10
$R^4 =$ H or $CH_3$;
$R^1 = —(CH_2)_o—$, with o=0 to 18, $—CH_2—O—R^5—O—CH_2—$, where $R^5 =$

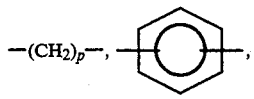

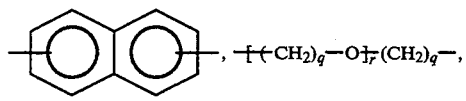

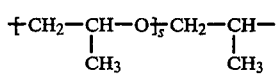

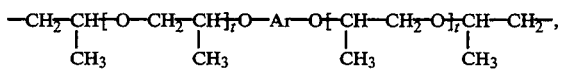

with p=2 to 20, q=2 to 4, r=1 to 50, s=0 to 50, t=0 to 25,
Ar=

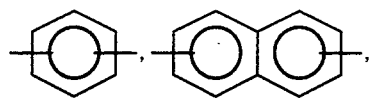

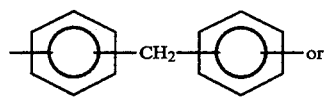

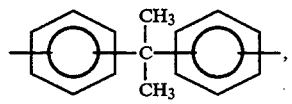

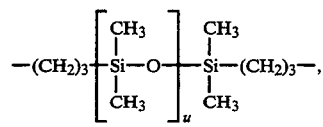

with u=0 to 150, or the corresponding grouping from 3,4-epoxycyclohexylmethyl-3',4'-epoxycyclohexane carboxylate, i.e., the compound:

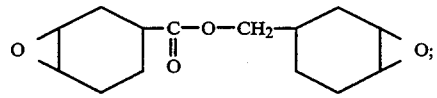

$R^2 = —(CH_2—CH=CH—CH_2)_n—$, $—R^6—$, $—R^6—O—CO—R^7—CO—O—R^6—$ or

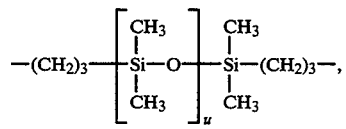

where n=1 to 50, u=0 to 150,
$R^6$ has the same meaning as $R^5$, except

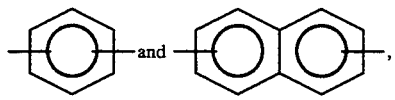

and
R$^7$ has the following meaning:

$$-(CH_2)_v-, \quad -(CH_2)_{q-1}-O+(CH_2)_q-O\!\!\!\!\!+_{\!\!\!s}(CH_2)_{q-1}-,$$

$$-(CH_2)_{q-1}+O-(CH_2)_q\!\!\!\!+_{\!\!\!t}O-Ar-O+(CH_2)_q-O\!\!\!\!+_{\!\!\!t}(CH_2)_{\overline{q-1}},$$

with q=2 to 4, s=0 to 50, t=0 to 25, v=0 to 20, and

Ar has the meaning indicated above.

The polyethers according to the invention are epoxyfunctional polyether resins that can be cured with radiation; such compounds have not been known until now. These compounds demonstrate the advantageous properties of polyethers in their cured state, and, if they contain urethane groupings, also the advantageous properties of polyurethanes. Because of the presence of the epoxy groups, it is also possible to modify the cured resins and thus to vary their properties. It is advantageous if curing of the polyether resins according to the invention is carried out by irradiation, since structuring is possible in this way; in this connection, substrates in layer form are used.

The new epoxyfunctional polyethers are produced in such a manner that first, α,ω-diepoxides with the general formula $$CH_2\!\!-\!\!CH\!\!-\!\!R^1\!\!-\!\!CH\!\!-\!\!CH_2,$$
$$\diagdown\!\!\diagup \qquad \diagdown\!\!\diagup$$
$$O \qquad\qquad O$$

where R$^1$ has the meaning indicated above, are brought to reaction with α,ω-diols with the general formula

HO—R$^2$—OH where R$^2$ has the meaning indicated above, in a molar ratio of 2:1, at temperatures ≦70° C., in the presence of a catalyst. This results in the formation of 2:1 adducts containing hydroxyl groups, with the following structure:

$$CH_2\!-\!CH\!-\!R^1\!-\!CH\!-\!CH_2\!-\!O\!-\!R^2\!-\!O\!-\!CH_2\!-\!CH\!-\!R^1\!-\!CH\!-\!CH_2.$$
$$\diagdown\!\!\diagup \qquad\quad | \qquad\qquad\qquad\qquad | \qquad\quad \diagdown\!\!\diagup$$
$$O \qquad\quad O \qquad\qquad\qquad\qquad O \qquad\quad O$$
$$\qquad\quad\; H \qquad\qquad\qquad\qquad\; H$$

To adjust the 2:1 adducts to be curable, their OH groups are reacted with cross-linking groups that can be polymerized with radicals, specifically under such reaction conditions that the epoxy groups are maintained, i.e., are not changed. When this is done, epoxyfunctional polyether resins with cross-linking groups that can be cured with radicals are formed. To introduce the cross-linking groups, the following compounds, in particular, can be used: isocyanatoalkyl (meth)acrylate, (meth)acrylic acid chloride or anhydride, cinnamic acid chloride and carboxylic acid chlorides containing maleinimide groups.

The following compounds are used as α,ω-diepoxides:
aliphatic diepoxides;
aliphatic, aromatic and aliphatic/aromatic diglycidyl ethers, which can contain hetero atoms, such as O, in the main chain;
cycloaliphatic diepoxides, such as 3,4-epoxycyclohexylmethyl-3′,4′-epoxycyclohexane carboxylate;
silicon-organic diepoxides.

The following compounds serve as α,ω-diols:
α,ω-alkane diols;
α,ω-hydroxy-terminated polyethers;
α,ω-hydroxy-terminated polyesters;
α,ω-hydroxyalkyl-terminated polysiloxanes;
α,ω-hydroxy-terminated polybutadiene.

The reaction of the diols with the diepoxides, which is carried out in an inert solvent or in substance, generally takes place in the presence of a strong organic acid, such as trifluoromethane sulfonic acid, as the catalyst. For this purpose, however, a poly(perfluoroalkylene) sulfonic acid, for example, can also be used. During the subsequent reaction of the 2:1 adducts containing hydroxyl groups with the compound containing the group which can be cross-linked with radicals, a catalyst is also used. In the case of isocyanates, this is a Lewis acid, for example dibutyl tin dilaurate. In the case of acid anhydrides, N-methyl imidazole can serve for this purpose. In the reaction with carboxylic acid chlorides, organic bases, such as pyridine or quinoline, can be used as acid acceptor and catalyst.

The epoxyfunctional polyether resins produced in this manner, which have double bonds, can be applied according to ordinary methods, such as spin-coating, roller-coating or curtain-coating, spreading and electrostatic coating. The layer thickness can be controlled by adjusting the viscosity, if necessary by adding solvents or reactive diluents. The olefinic-unsaturated resins which contain epoxy groups can be cured with radicals, where the cured layers still have epoxy groups. The resins can be cross-linked using UV or structured, particularly after addition of a photoinitiator. The properties of the cured or structured layers, such as cross-linking density, swelling behavior and polarity, can be varied over a broad range, via the remainder R$^1$ (of the α,ω-epoxides) and via the remainder R$^2$ (of the α,ω-diols).

Modification of the resins, i.e., coupling of function carriers to the cured or structured layers, is easily possible via the epoxy groups which are present. The polyethers according to the invention can be modified in such a way that they can be used as biocompatible plastics or in membranes for biosensors and chemosensors.

The method according to the invention offers the following advantages:

It allows immobilization of all biochemical substances which have reactive NH, OH, SH or COOH groups at their periphery.

Layers produced according to this method, with immobilized biochemical substances, can also be stored dry and under non-sterile conditions, without any damage to these substances.

Immobilization of the biochemical substances takes place under very mild conditions, in aqueous solution and in the absence of reactive components with a low molecular weight; in this way losses, for example as the result of enzyme denaturing, are avoided.

A relatively small number of polymer materials with great chemical and thermal stability, which can be produced on a large technical scale and which are therefore accessible at low cost, is used for immobilization of a large number of different types of biochemical substances.

The production and cross-linking of the layers can be carried out in technically simple, reproducible and low-cost manner. When using goods which run to length as the carrier, such as films, textiles, hoses and strips, continuous methods of operation can be used.

Immobilization of the biochemical substances can take place independent of the layer production, depending on the need and intended use, if necessary not until just before use, to be carried out by the user.

Desorption, migration and extraction losses are avoided by chemical anchoring of the biochemical substances in the polymer matrix.

By the formation of covalent bonds between the peripheral NH, OH, SH and COOH groups of the biochemical substances and the very soft and flexible sheathing polymer material, the substances, some of which are very sensitive, for example enzymes, are given great functional and long-term stability.

The production of very thin layers ($<<1$ μm) allows very short diffusion paths for reaction partners and products.

Since size, shape, hydrophilicity and reactivity of the biochemical substances to be immobilized play a large role in the method according to the invention, the immobilization is connected with a certain selection and cleaning; this allows the use of low-cost products with low activity in many cases.

The method according to the invention can be used technically anywhere where immobilized biochemical substances are already in use today, or where they could be advantageously used. This method offers particular advantages for use in enzyme reactors, such as those used on a technical scale for the production of L-amino acids from acetyl-DL-amino acids, α-ketocarboxylic acids, α-hydroxycarboxylic acids or α,β-unsaturated carboxylic acids, for the production of L-malic acid from fumaric acid, for isomerization of glucose as well as for penicillin derivatization. In this connection, the immobilization of the enzymes required can take place in thin layers, on very different materials. Aside from various metals and metal oxides, a large number of different plastics are also possible materials. Immobilization in layers on porous membranes offers special advantages for use in membrane reactors.

Use of the method according to the invention also brings advantages in the identification, separation and cleaning of biochemical materials. In analysis, use within the scope of affinity chromatography, in particular, offers interesting application possibilities. In medicine, the method according to the invention can be used for intracorporeal and extracorporeal enzyme therapy and for the production of artificial organs, for example artificial kidneys. By immobilization of certain biochemical substances, such as heparin, the biocompatibility of the polyether layers can be increased, so that these can serve as the coating for implants, for example.

The invention will be explained in more detail, by the following examples which should be regarded in an illustration rather than a restriction sense.

EXAMPLES 1 TO 6

In a 500 ml three-neck flask (with stirrer, interior thermometer, Anschütz cap, dropping funnel and reflux condenser with drying tube), 46 mmole α, ω-diol (see Table 1) are placed, together with 50 g dry chloroform (stabilized with 2-methyl butene-2), and mixed with 20 drops trifluoromethane sulfonic acid. Then the apparatus is flooded with argon and the flask contents are heated to 60° C. At this temperature, 92 mmole diepoxide (see Table 1), dissolved in 100 g dry chloroform, are added within approximately 30 min, while stirring.

The reaction is continued to a residual epoxide content of 50% (see Table 1). After the end of the reaction, the heating bath is removed, then 10 g cross-linked poly-4-vinyl pyridine are added to neutralize the catalyst. Then the reaction mixture is allowed to cool down, while stirring. After 2 hours of stirring, the poly-4-vinyl pyridine is removed by pressure filtration via an 8 μm membrane filter; the reaction product remains in solution for further processing.

After balancing out the chloroform losses caused by processing, the resin solution is mixed with 20 drops dibutyl tin dilaurate solution (10 g dibutyl tin dilaurate in 100 ml chloroform) as the catalyst and with 200 mg each of hydroquinone and 2,6-di-tert.-butyl-4-methyl phenol. 14.3 g isocyanatoethyl methacrylate (92 mmole) are then dripped in within approximately 1 h, while stirring; the interior temperature is not allowed to exceed 30° C. during this time. The reaction mixture is stirred further at room temperature, until the isocyanate has completely converted, then the solvent is removed at room temperature, first in water jet pump vacuum and then in oil diffusion pump vacuum. A clear, viscous resin is obtained (see Table 1).

EXAMPLE 7

100 parts by weight of the epoxyfunctional resin which can be radiation-cured with radicals or structured, according to Example 1, are mixed with 7 parts by weight of the commercially available reactive diluent oligotriacrylate and with 2 parts by weight of the commercially available photoinitiator 2-hydroxy-2-methyl-1-phenyl propan-1-one and mixed thoroughly. A resin layer with a thickness of approximately 100 μm is poured from the mixture, and this is irradiated under nitrogen, in a commercial UV irradiation system, for 3.2 s. A clear, colorless, non-sticky cured film with an epoxide content of 90 mmole/100 g is obtained.

TABLE 1

| Example | α,ω-diol | α,ω-diepoxide | Reaction time (50% residual epoxide) | Yield | Epoxide, Content mmole/100 g |
| --- | --- | --- | --- | --- | --- |
| 1 | 1,4-butane diol (4.1 g) | PTHF-diglycidyl ether*) (80 g) | 14 h | 85 g (85%) | 92 |
| 2 | 1,6-hexane diol (5.4 g) | PTHF-diglycidyl ether*) (80 g) | 14 h | 85 g (85%) | 90 |
| 3 | polytetrahydro-furan-250 (11.5 g) | PTHF-diglycidyl ether*) (80 g) | 12 h | 87 g (82%) | 85 |
| 4 | THF/EO-copoether-glycol**) (57.5 g) | PTHF-diglycidyl ether*) (80 g) | 15 h | 21 g (80%) | 59 |
| 5 | polytetrahydro-furan-250 (11.5 g) | 1,2,7,8-diepoxy octane (13.1 g) | 10 h | 33 g (85%) | 232 |
| 6 | 1,4-butane diol (4.1 g) | α,ω-diglycidoxypropyl polydimethyl | 15 h | 85 g (80%) | 85 |

TABLE 1-continued

| Example | α,ω-diol | α,ω-diepoxide | Reaction time (50% residual epoxide) | Yield | Epoxide, Content mmole/100 g |
|---------|----------|---------------|--------------------------------------|-------|------------------------------|
|         |          | disiloxane (87.5 g) |                                |       |                              |

*polytetrahydrofuran diglycidyl ether ($M_n$ = 870 g/mole)
**tetrahydrofuran/ethylene oxide copolyether glycol —

EXAMPLE 8

Production of Polyether/Enzyme Layers 100 parts by mass of an epoxyfunctional polyether with the structure

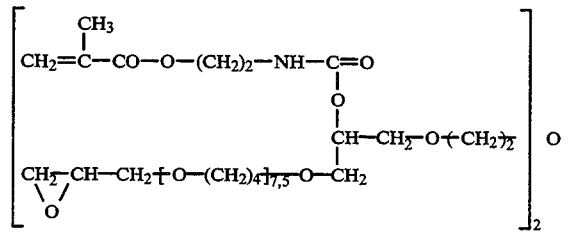

are mixed with 7 parts by mass propoxylated glycerol triacrylate as the reactive diluent and 2 parts by mass 2-hydroxy-2-methyl-1-phenyl propan-1-one as the photoinitiator, and mixed with the corresponding amount of toluene to adjust the desired processing properties. This solution is then applied to the surface of the carrier material, which has been pretreated with an adhesion agent, if necessary, by dipping, dripping or spreading. Parallel to this, silicon wafers are coated with the same solution, using a varnish centrifuge; the centrifuge time is approximately 10 s.

The layers are dried in a laminar box and subsequently cross-linked under nitrogen, by UV irradiation (System F 450 of the company Fusion UV-Curing Systems) in a wavelength range of 200 to 450 nm; irradiation period: 4.6 s. To remove soluble components, the cross-linked layers are extracted with dioxane for 24 h, at room temperature. To increase the hydrophilicity of the layers, part of the epoxy groups is reacted with compounds containing NH groups, in the form of amino acids. In this connection, storage of the layers in a 2% solution of proline or glutaminic acid in a 2:1 mixture of dioxane and water at 40° to 60° C. has particularly proven to be effective. Using silicon wafers treated in a corresponding manner, the conversion can be followed by IR spectroscopy. A conversion of 50% is sufficient in most cases; if needed, however, higher values can also be adjusted.

Immobilization of the enzymes takes place by incubation of the layers in an approximately 1 to 2% solution of the enzyme in water at 20° to 30° C. To accelerate this process, the solution can be mixed with 10 to 50% dioxane, depending on the sensitivity of the enzyme. Immobilization is complete after 1 to 8 h. Remaining epoxy groups can be eliminated by gentle conversion with amino acids. As the last step, the layers are freed from extractable components by being intensively washed with water.

Table 2 contains a summary of the enzymes immobilized according to the invention, in identically pretreated layers with a thickness of 10 μm, on silicon wafers, immobilized at 30° C. within 8 h, as well as the enzyme activity at 25° C.

EXAMPLE 9

Influence of the Enzyme Activity on the Activity of Polyether/Enzyme Layers

A polyether layer produced on a filter paper according to Example 8, with a thickness of approximately 20 μm, is incubated for 6 h at 60° C., in a 2% solution of proline in a 2:1 mixture of dioxane and water, after UV cross-linking and extraction with dioxane. The filter paper is divided, and the one half is treated with a 2% aqueous solution of glucose oxidase with an activity of 22 U/mg, and the other half is treated with a 2% aqueous solution of glucose oxidase with an activity of 276 U/mg, each for 8 h at 30° C. Both halves are then watered separately for 24 h.

TABLE 2

| Enzyme | Activity | Determination Method |
|--------|----------|----------------------|
| Glucose oxidase from *Aspergillus niger*, lyophil. 240 U/mg | 0.8 U/cm² | Gluc-DH Method of the Merck company |
| Catalase from cattle liver, suspension 65,000 U/mg | 350 U/cm² | See: B. Stellmach, "Determination Methods for Enzymes", Steinkopff-Verlag, Darmstadt 1988, pages 152 to 155 |
| Urease from broad beans, lyophil. 100 U/mg | 0.7 U/cm² | See: B. Stellmach, "Determination Methods for Enzymes", Steinkopff-Verlag, Darmstadt 1988, pages 269 to 271 |
| Alcohol dehydrogenase from yeast, lyophil. 400 U/mg | 2.0 U/cm² | See: B. Stellmach, "Determination Methods for Enzymes", Steinkopff-Verlag, Darmstadt 1988, pages 11 and 12 |
| L-asparaginase, 50% solution in glycerol 80 U/mg solution | 0.6 U/cm² | See: B. Stellmach, "Determination Methods for Enzymes", Steinkopff-Verlag, Darmstadt 1988, pages 63 to 68 |

Subsequently, samples with a size of 1 cm² of the two halves are examined for activity by means of the Gluc-DH method. For the first half, a mean activity of 1.6 U/cm² is determined, while for the second half, a mean activity of 1.7 U/cm² is determined. This result shows that the activity of the polyether/enzyme layers is practically independent of the activity of the enzyme used.

EXAMPLE 10

Production of Polyether Layers for Immobilization of Enzymes on Various Carrier Materials The mixture of epoxyfunctional polyether, reactive diluent and photoinitiator described in Example 8 is dissolved in different amounts of toluene. The solutions obtained are applied to different carrier materials, described in greater detail in Table 3, by means of dipping (=D) or spin-coating (=S). Solid materials are first polished and cleaned on their surface, and coated by means of spin-coating, if necessary after pretreatment with an adhesion agent; the centrifuge time is 10 s. Films, membranes and non-wovens are either glued onto a solid carrier and coated by means of spin-coating or dipped. Woven textiles are coated by means of dipping and subsequently stripping or pressing the excess polyether off. All layers are cross-linked by means of UV-radiation, as described in Example 8.

Table 3 contains a summary of the materials and coating techniques used, as well as the polyether layer thicknesses. The adhesion of the layers to the carrier material was determined by 24-hour storage and swelling in dioxane. The layers can be utilized for immobilization of enzymes, as described in Example 8.

EXAMPLE 11

Evaluation of the Effectiveness of Polyether/Enzyme Layers

Analogous to Example 10, a layer of the polyether described in Example 8, with a thickness of approximately 10 μm, is produced on a polyester membrane with a layer thickness of 14 μm, by means of spin-coating. Corresponding to Example 8, this composite is treated with proline for 6 h at 60° C., and is then treated for 6 h at 30° C. with an aqueous enzyme solution. The following enzymes are immobilized: fumarase, activity 200 U/mg; L-aspartase, activity 5 U/mg.

Fumarase catalyzes the conversion of fumaric acid with water to L-malic acid, L-aspartase catalyzes the conversion of fumaric acid with ammonia to L-asparaginic acid. Since both enzymes also catalyze the reverse reaction in each case, an excess of initial components is used. The conversion in the presence of fumarase takes place at a pH of 7.5, while the conversion in the presence of L-aspartase takes place at a pH of 8.5. The decrease in fumaric acid concentration is determined by iodometry (see in this regard: "Chem. Ber." ["Chemical Reports"], Vol. 70 (1937), pages 903 to 907).

The two conversions are carried out in such a manner that the one time, approximately 10 cm² of the membrane containing aspartase is placed in 200 ml of a solution of 2% fumaric acid and 2% ammonia (NH₄OH), and the other time, approximately 1 cm² of the membrane containing fumarase is placed in 400 ml of a solution of 2% fumaric acid, and the solutions are stirred. In order to avoid strong changes in concentration, the reaction is interrupted after 24 h in each case, the fumaric acid concentration is determined and the reaction solution is replaced with a freshly prepared solution.

The conversion curves determined show that the activity of the two enzymes is practically not reduced over a period of 5 days.

TABLE 3

| Carrier material | Adhesion agent | Coating technique | Layer thickness (μm) | Adhesion |
|---|---|---|---|---|
| Silicon* | — | S | 0.1-50 | — |
|  | + | S | 0.1-50 | + |
| Quartz* | — | S | 0.1-50 | — |
|  | + | S | 0.1-50 | + |
| Epoxy resin* | — | S | 0.1-50 | + |
|  | + | S | 0.1-50 | + |
| Polyether ether ketone* | — | S | 0.1-30 | + |
| Polysiloxane layer on silicon* | — | S | 0.1-30 | + |
| Polyester membrane | — | S | 0.1-30 | + |
| Cellulose membrane | — | S | 0.1-30 | + |
| Cellulose filter paper | — | D | 50-150 | + |
| Acetyl cellulose membrane | — | S | 0.1-50 | + |
| Nylon 6,6 woven textile | — | D | 100-150 | + |
| Fiberglass woven textile | — | D | 100-200 | + |

(* = in wafer form)

What is claimed is:

1. A method for immobilization of a biochemical substance comprising the steps of:

applying an olefinic-unsaturated, epoxyfunctional polyether to a carrier material in the form of a layer, cross-linking the polyether by means of high-energy radiation or using peroxide, to form an epoxyfunctional polymer matrix, treating the layer with an aqueous solution of the biochemical substance, whereby the biochemical substance is immobilized in the polymer matrix by reaction with epoxy groups, and stabilizing the layer by reaction of non-reacted epoxy groups with a compound containing an amino group, a carboxyl group or an amino group and a carboxyl group, wherein the polyether has the structure

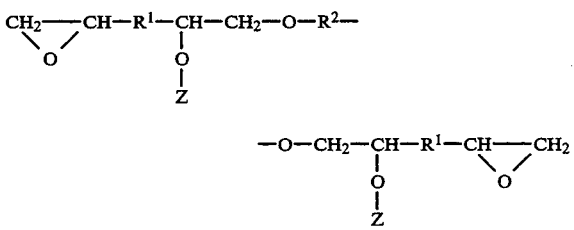

where the following applies:

Z=

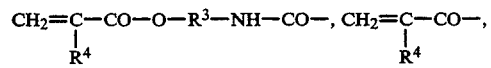

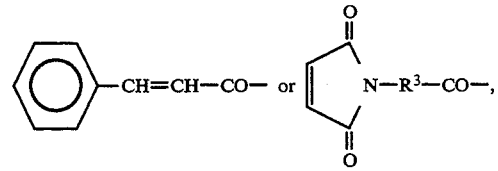

where
$R^3 = -(CH_2)_m-$, with m=1 to 10
$R^4 = H$ or $CH_3$;
$R^1 =$

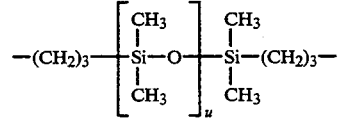

with u=0 to 150, $-(CH_2)_o-$, with o=0 to 18, or $-CH_2-O-R^5-O-CH_2-$, where $R^5 =$

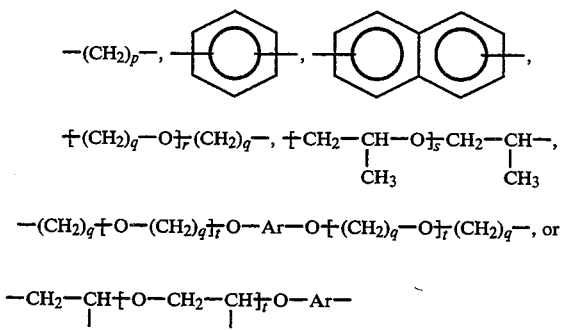

with p=2 to 20, q=2 to 4, r=1 to 50, s=0 to 50, t=0 to 25,
Ar=

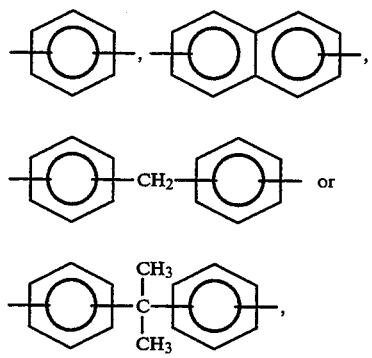

$R^2 = -(CH_2-CH=CH-CH_2)_n-$, $-R^6-$, $-R^6-O-CO-R^7-CO-O-R^6-$ or

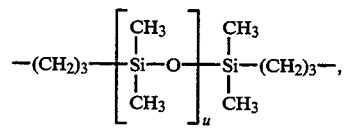

where n=1 to 50, u=0 to 150,
$R^6$ has the same meaning as $R^5$, except that

are excluded, and
$R^7$ has the following meaning:

$-(CH_2)_v-$, $-(CH_2)_{q-1}-O+(CH_2)_q-O\frac{1}{s}(CH_2)_{q-1}-$, or $-(CH_2)_{q-1}+O-(CH_2)_q\frac{1}{t}O-Ar-O+(CH_2)_q-O\frac{1}{t}(CH_2)_{q-1}$, with q=2 to 4, s=0 to 50, t=0 to 25, v=0 to 20, and Ar has the meaning indicated above.

2. The method according to claim 1 further comprising the step of hydrophilizing the polyether after cross-linking and before immobilizing the biochemical substance, by reacting some of the epoxy groups of the polyether with a hydrophilic compound.

3. The method according to claim 1 wherein the biochemical substance is an enzyme.

4. The method according to claim 2 wherein the biochemical substance is an enzyme.

5. The method according to claim 1 wherein the layer is stabilized with an amino acid.

6. The method according to claim 2 wherein the layer is stabilized with an amino acid.

7. The method according to claim 2 wherein the polyether is hydrophilized with an amino acid.

8. The method according to claim 4 wherein the polyether is hydrophilized with an amino acid.

9. The method according to claim 6 wherein the polyether is hydrophilized with an amino acid.

10. A method for immobilization of a biochemical substance comprising the steps of:

applying an olefinic-unsaturated, epoxyfunctional polyether to a carrier material in the form of a layer, cross-linking the polyether by means of high-energy radiation or using peroxide, to form an epoxyfunctional polymer matrix, treating the layer with an aqueous solution of the biochemical substance, whereby the biochemical substance is immobilized in the polymer matrix by reaction with epoxy groups.

and stabilizing the layer by reaction of non-reacted epoxy groups with a compound containing an amino group, a carboxyl group or an amino group and a carboxyl group, wherein the polyether has the structure $$R^1-O-R^2-O-R^1$$

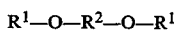

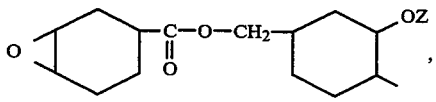

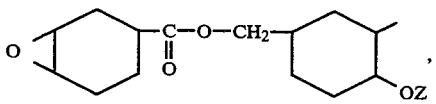

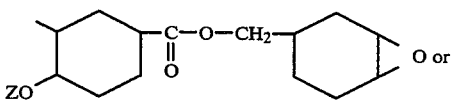

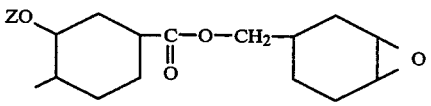

where the following applies:
Z=

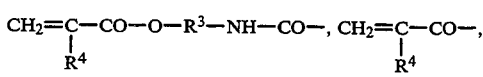

-continued

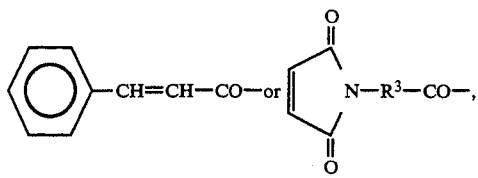

where $R^3 = -(CH_2)_m-$, with m=1 to 10

$R^4 =$ H or $CH_3$;

$R^2 = -(CH_2-CH=CH-CH_2)_n-$, $-R^5-$, $-R^5-O-CO-R^6-CO-O-R^5-$ or

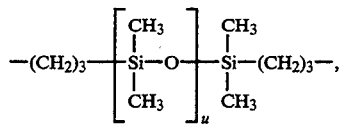

where n=1 to 50, u=0 to 150, $R^6 =$

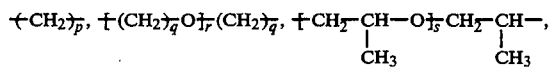

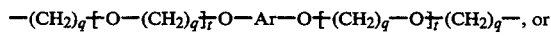

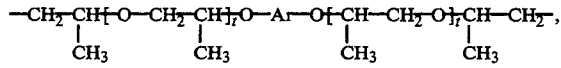

with p=2 to 20, q=2 to 4, r=1 to 50, s=0 to 50, t=0 to 25,

Ar=

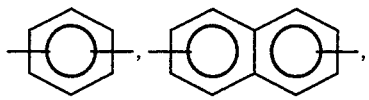

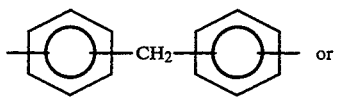

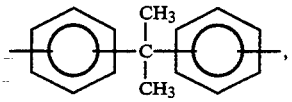

and $R^6$ has the following meaning:

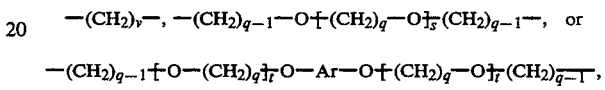

$-(CH_2)_{q-1}+O-(CH_2)_q\overline{)_t}O-Ar-O+(CH_2)_q-O\overline{)_t}(CH_2)_{q-1}-$, with q=2 to 4, s=0 to 50, t=0 to 25, v=0 to 20, and Ar has the meaning indicated above.

11. The method according to claim 10 further comprising the step of hydrophilizing the polyether after cross-linking and before immobilizing the biochemical substance, by reacting some of the epoxy groups of the polyether with a hydrophilic compound.

12. The method according to claim 10 wherein the biochemical substance is an enzyme.

13. The method according to claim 11 wherein the biochemical substance is an enzyme.

14. The method according to claim 10 wherein the layer is stabilized with an amino acid.

15. The method according to claim 11 wherein the layer is stabilized with an amino acid.

16. The method according to claim 11 wherein the polyether is hydrophilized with an amino acid.

17. The method according to claim 13 wherein the polyether is hydrophilized with an amino acid.

18. The method according to claim 15 wherein the polyether is hydrophilized with an amino acid.

* * * * *